(12) United States Patent
Foster et al.

(10) Patent No.: US 8,632,779 B2
(45) Date of Patent: Jan. 21, 2014

(54) S. AUREUS POLYPEPTIDES AND ANTIBODIES

(75) Inventors: Simon J. Foster, Hathersage (GB); Jorge Garcia-Lara, Sheffield (GB)

(73) Assignee: Absynth Biologics Limited, Sheffield (GB)

(*) Notice: Subject to any disclaimer, the term of this patent is extended or adjusted under 35 U.S.C. 154(b) by 82 days.

(21) Appl. No.: 13/420,497

(22) Filed: Mar. 14, 2012

(65) Prior Publication Data

US 2012/0171214 A1 Jul. 5, 2012

Related U.S. Application Data

(60) Division of application No. 12/826,160, filed on Jun. 29, 2010, now Pat. No. 8,163,288, which is a continuation of application No. 11/909,258, filed as application No. PCT/GB2006/000826 on Mar. 8, 2006, now Pat. No. 7,767,211.

(30) Foreign Application Priority Data

Mar. 23, 2005 (GB) .................................. 0505949.8

(51) Int. Cl.
*A61K 39/40* (2006.01)
*A61K 39/395* (2006.01)
*C12P 21/08* (2006.01)

(52) U.S. Cl.
USPC .................. 424/165.1; 424/139.1; 424/141.1; 435/70.2; 435/70.21

(58) Field of Classification Search
None
See application file for complete search history.

(56) References Cited

U.S. PATENT DOCUMENTS 6,627,747 B1  9/2003  Fritz et al.
7,608,276 B2 * 10/2009  Masignani et al. ........ 424/243.1

FOREIGN PATENT DOCUMENTS

| WO | 00/13694 A1 | 3/2000 |
| WO | 00/14200 A2 | 3/2000 |
| WO | 01/70955 A2 | 9/2001 |
| WO | 02/077183 A2 | 10/2002 |

OTHER PUBLICATIONS

Rudikoff et al (Proc. Natl. Acad. Sci. USA, 79(6):1979-1983, Mar. 1982).*
Colman P. M. (Research in Immunology, 145:33-36, 994).*
Paul, Fundamental Immunology, 3rd Edition, 1993, pp. 292-295.*
Li et al (Proc. Natl. Acad. Sci. USA 77:3212-3214, 1980).*
Lederman et al (Molecular Immunology 28:1271-1281, 1991).*
Kovalic, D.K., et al., "Nucleic Acid Molecules and Other Molecules Associated with Plants and Uses Thereof for Plant Improvement;" Sequence 203703 from US Patent No. 7214786, NCBI Database Accession No. ABU16234 (Aug. 10, 2007).
Kovalic, D.K., et al., "Nucleic Acid Molecules and Other Molecules Associated with Plants and Uses Thereof for Plant Improvement;" Sequence 204024 from US Patent No. 7214786, NCBI Database Accession No. ABU16555 (Aug. 10, 2007).
Gill, S.R., et al., "Insights on Evolution of Virulence and Resistance from the Complete Genome Analysis of an Early Methicillin-Resistant *Staphylococcus aureus* Strain and a Biofilm-Producing Methicillin-Resistant *Staphylococcus epidermidis* Strain;" J. Bacteriol. vol. 187, No. 7, pp. 2426-2438, NCBI Database Accession No. YP_186241 (Jul. 18, 2008).

* cited by examiner

*Primary Examiner* — Padma V Baskar
(74) *Attorney, Agent, or Firm* — Janet Sleath; Speckman Law Group PLLC

(57) ABSTRACT

The invention relates to antigenic polypeptides expressed by pathogenic microbes, vaccines comprising said polypeptides; therapeutic antibodies directed to said polypeptides and methods to manufacture said polypeptides, vaccines and antibodies.

9 Claims, 10 Drawing Sheets

Fig. 1 atgggtaaacctgtcgtagccattgtcgggagaccaaatgtaggaaaatccacaatcttt
aaccggattgcgggagaaagaatttcaatagtagaagatacccctggcgtgacaagggat
cggatatacagctcggctgaatggctgaattatgattttaatttgattgatacgggcggt
attgatatcggtgatgagccgttttagcgcagattcgccagcaagctgaaatcgccatg
gatgaagcggacgtgattatttttatggtgaacggccgtgaaggcgtgacagctgctgat
gaagaagtggcgaaaattttgtaccgcacaaaaaagcctgttgttttagcggttaataaa
ctggataacacagaaatgagagcgaatatttatgattttattcgctaggctttggcgag
ccgtatccaatttcgggaacacacggactcggactgggtgatttactggatgccgttgca
gagcattttaaaaacattcctgaaacgaaatacaatgaagaagttattcaattctgtctg
atcggacgtccaaatgtcggaaagtcttcacttgtgaatgcgatgctcggcgaagaacgc
gttattgtcagcaacgtggctggaacgacaagagatgctgttgatacgtcatttacttac
aaccagcaggagtttgtcattgtcgatactgcaggtatgcgaaaaaaagggaaagtctat
gaaacgactgagaagtatagtgtactgcgggcgctaaaagcgattgaccgctcagaagtc
gtggcggttgtgctggatggcgaagaaggcattattgaacaggacaagcgtatcgccggt
tatgcacacgaagcgggcaaggccgtcgtcatcgtcgtaaacaaatgggatgctgttgac
aaagatgagagcacgatgaaagaatttgaagaaatattcgcgatcattttcaatttctg
gattatgcgccaatcctatttatgtctgccttaacgaaaaaacggatccatactctgatg
cctgcgattatcaaagctagtgaaaatcattcacttcgagttcaaacaaacgtcttaaat
gatgtcatcatggacgctgtggcaatgaatccgacaccgactcataacggttctcgtttg
aaaatttactatgcgactcaagtgtcggtaaagccgccaagcttcgttgtgtttgtaaac
gatccggaactgatgcattttcatacgaacggttttagaaaaccgaatcagagacgcg
ttcggttttgaggggacaccaatcaaaatatttgcaagagctagaaaa

Fig. 2 atgaaagtcacaaagtcagaaatcgtgatcagtgcagtaaaaccggaacagtaccctgaa ggggggcttccggaaatcgcattggccggaagatcgaacgtaggaaaatcgtctttatc aattcattaatcaatcgcaaaaatcttgcgagaacgtcatcaaagccgggaaaaacacaa acgcttaatttctacattatcaatgatgagctgcattttgtggatgtgccgggctacggt tttgccaaagtgtcaaagtctgagcgtgaagcatggggcagaatgattgaaacctatatc acgacacgcgaggaattaaaagctgtggtgcagatcgttgatttgcggcatgcgccatct aatgatgatgtacagatgtatgaattttaaagtattacggcattcctgttattgttatc gctacaaaggcggataagatcccgaaaggtaaatgggacaaacacgcgaaggttgtccga caaacattaaatattgatccggaagacgagctgatcctcttttcttcagaaacgaaaaag ggaaaagacgaagcttggggagcgatcaaaaaaatgataaaccgg

Fig. 3 atgaaaacgaaaagatggtttgtggatgtaactgacgagttatccacaaatgatccacaa attgcacaagcagccgctttgctccgagaaaatgaggtcgttgcctttccgacagaaaca gtatatggcctaggcgcaaacgcaaaaaatacggatgccgtcaaaaaaatatatgaggcg aaagggcggccgagcgataatcccctgattgtccacattgcggatatcagccagcttgag gatttaacgggcccggcgccggaaaaggcgaaaacattgatgaaacggttttggccggga gcacttacgctcattctgccttgcaaacctgatgcgctttcacctcgtgtaacggcaggt cttgaaacggttgccattagaatgccggatcatccgcttgcccttgcattgattcgcgaa tcgggactgccgattgcagcaccgagcgccaatctatcaggcaagccaagtcccacaaaa gcggagcatgtggctcacgacttggatggccgcatagccggtattgtggatggaggccct accggaatcggggtcgaatcaactgtgctttcatgtgcggacgacatccctgttctcttg cgtcctggcggcattacgaaggaacaaattgaagcggtgatcgggccgatccatgtggat aaagggctcagcgaccaaaacgagaagccgatttctccagggatgaaatatacacattat gcgccgacagcgcctcttgccatttgcgaaggcagcccagagcgcattcagcacctcatt caagaatatcaacagggtggaagacgggtcggtgtcctgacgacagaagaaaaagcgggc gtttattccgctgattatgtgaagagctgcggaagacgggctcagcttgagactgttgcg gcagggctgtatgatgctttgcgcagctttgatgagaataaggtggatttcattatagcg gaatcctttccggatacaggtgtcggtcttgctattatgaacaggctgatgaaagccgcc ggaggaagagtgattcgc

Fig. 4 ttaccagttcacgcagatggccctattagt

Fig. 5 ttgaagattttaaatatgtttctttagca

Fig. 6A atgactaaagatatattaatactagctgttgaaacaagttgtgatgaaacaagcgttagt
gttataaaaaatggcagagatattttatcaaatacagttttaagtcagattgaaagtcat
aaacgatttggcggtgtcgttcccgaagtggcaagtagacatcacgttgaaggtataaca
acaacaataaacgaggctctagtggatgccgatgtatcaatggaagatattgatgccata
gcggttaca

Fig. 6B atgactaaagatatattaatactagctgttgaaacaagttgtgatgaaacaagcgttagt
gttataaaaaatggcagagatattttatcaaatacagttttaagtcagattgaaagtcat
aaacgatttggcggtgtcgttcccgaagtggcaagtagacatcacgttgaaggtataaca
acaacaataaacgaggctctagtggatgccgatgtatcaatggaagatattgatgccata
gcggttacagaaggccctggactaattggtgcgttactaataggtgttaatgcagccaaa
gcattggcatttgcttacgataagccacttattcctgttcatcatattgcaggacatata
tatgctaatcacatagaagagccattaacattcccgctaattgcacttattgtttcaggt
ggacatactgaattagtttatatgaaagatcatttatcatttgaagtcattggtgaaaca
cgagatgacgcagtaggtgaggcttatgataaagtggcacgaacaattggtttaaattat
ccaggtggtccacaagttgatcggttggctgctgaaggtgaagatacttattcattccct
cgtgtttggttggataaagatagttatgattttagttttagtgggttgaaaagtgccgtg
atcaatcaacttcacaatcaacgacaaaaaaatattccaatcattgaagctaacgtagca
acgagctttcaaaatagtgttgtagaggtgcttacgtttaaagctattcaagcttgtaaa
gaatatagtgttcagcgattaattgttgctggtggcgtggcgagtaataaaggattacgt
caatctttagcggatcaatgcaaagtcaatgacattcaattaactatcccaagtcctaaa
ttatgcacagataatgctgcaatgataggcgttgccggccactctttgtatcagcaaggt
cgatttgctgatttagcattaaatgggcacagcaatatagatttagaagagtattctgca
gaataa

Fig. 7

MGKPVVAIVGRPNVGKSTIFNRIAGERISIVEDTPGVTRDRIYSSAEWLNYDFNLIDTGG
IDIGDEPFLAQIRQQAEIAMDEADVIIFMVNGREGVTAADEEVAKILYRTKKPVVLAVNK
LDNTEMRANIYDFYSLGFGEPYPISGTHGLGLGDLLDAVAEHFKNIPETKYNEEVIQFCL
IGRPNVGKSSLVNAMLGEERVIVSNVAGTTRDAVDTSFTYNQQEFVIVDTAGMRKKGKVY
ETTEKYSVLRALKAIDRSEVVAVVLDGEEGIIEQDKRIAGYAHEAGKAVVIVVNKWDAVD
KDESTMKEFEENIRDHFQFLDYAPILFMSALTKKRIHTLMPAIIKASENHSLRVQTNVLN
DVIMDAVAMNPTPTHNGSRLKIYYATQVSVKPPSFVVFVNDPELMHFSYERFLENRIRDA
FGFEGTPIKIFARARK

Fig. 8

MKVTKSEIVISAVKPEQYPEGGLPEIALAGRSNVGKSSFINSLINRKNLARTSSKPGKTQ
TLNFYIINDELHFVDVPGYGFAKVSKSEREAWGRMIETYITTREELKAVVQIVDLRHAPS
NDDVQMYEFLKYYGIPVIVIATKADKIPKGKWDKHAKVVRQTLNIDPEDELILFSSETKK
GKDEAWGAIKKMINR

Fig. 9

MKTKRWFVDVTDELSTNDPQIAQAAALLRENEVVAFPTETVYGLGANAKNTDAVKKIYEA
KGRPSDNPLIVHIADISQLEDLTGPAPEKAKTLMKRFWPGALTLILPCKPDALSPRVTAG
LETVAIRMPDHPLALALIRESGLPIAAPSANLSGKPSPTKAEHVAHDLDGRIAGIVDGGP
TGIGVESTVLSCADDIPVLLRPGGITKEQIEAVIGPIHVDKGLSDQNEKPISPGMKYTHY
APTAPLAICEGSPERIQHLIQEYQQGGRRVGVLTTEEKAGVYSADYVKSCGRRAQLETVA
AGLYDALRSFDENKVDFIIAESFPDTGVGLAIMNRLMKAAGGRVIR

Fig. 10

LPVHADGPIS

Fig. 11

LKIFKYVSLA

Fig. 12A

MTKDILILAVETSCDETSVSVIKNGRDILSNTVLSQIESHKRFGGVVPEVASRHHVEGITT
TINEALVDADVSMEDIDAIAVT

Fig. 12B

MTKDILILAVETSCDETSVSVIKNGRDILSNTVLSQIESHKRFGGVVPEVASRHHVEGIT
TTINEALVDADVSMEDIDAIAVTEGPGLIGALLIGVNAAKALAFAYDKPLIPVHHIAGHI
YANHIEEPLTFPLIALIVSGGHTELVYMKDHLSFEVIGETRDDAVGEAYDKVARTIGLNY
PGGPQVDRLAAEGEDTYSFPRVWLDKDSYDFSFSGLKSAVINQLHNQRQKNIPIIEANVA
TSFQNSVVEVLTFKAIQACKEYSVQRLIVAGGVASNKGLRQSLADQCKVNDIQLTIPSPK
LCTDNAAMIGVAGHSLYQQGRFADLALNGHSNIDLEEYSAE

S. AUREUS POLYPEPTIDES AND ANTIBODIES

REFERENCE TO RELATED APPLICATIONS

This application is a divisional of U.S. application Ser. No. 12/826,160 filed Jun. 29, 2010, now U.S. Pat. No. 8,163,288, issued Apr. 24, 2012, which is a continuation of U.S. application Ser. No. 11/909,258, filed Sep. 20, 2007, now U.S. Pat. No. 7,767,211 issued Aug. 3, 2010, which claims priority to International Application No. PCT/GB2006/000826, filed Mar. 8, 2006, which claims priority to United Kingdom Application No. GB 0505949.8, filed Mar. 23, 2005, the disclosures of which are hereby incorporated by reference.

FIELD OF THE INVENTION

The invention relates to antigenic polypeptides expressed by pathogenic microbes, vaccines and immunogenic compositions comprising the antigenic polypeptides and therapeutic antibodies directed to the antigenic polypeptides.

BACKGROUND

A problem facing current medical development is the evolution of antibiotic resistant strains of a number of significant pathogenic microbes. An example of a pathogenic organism which has developed resistance to antibiotics is *Staphylococcus aureus*. *S. aureus* is a bacterium whose normal habitat is the epithelial lining of the nose in about 20-40% of normal healthy people and is also commonly found on people's skin usually without causing harm. However, in certain circumstances, particularly when skin is damaged, this germ can cause infection. This is a particular problem in hospitals where patients may have surgical procedures and/or be taking immunosuppressive drugs. These patients are much more vulnerable to infection with *S. aureus* because of the treatment they have received. Resistant strains of *S. aureus* have arisen in recent years. Methicillin resistant strains are prevalent and many of these resistant strains are also resistant to several other antibiotics. Currently there is no effective vaccination procedure for *S. aureus*.

The present invention is concerned with the identification of potential vaccine components and therapies against which the problem of directly resistant pathogen strains is avoided or reduced.

Amongst the approximately 4100 genes in the soil gram-positive bacterium *Bacillus subtilis* chromosome, 271 are indispensable ("essential") for growth and among them, 23 have undefined roles in the physiology of the organism (gcp, obg, ppaC-yybQ-, trmU, yacA, yacM, ydiB, ydiC, yjbN, ykqC, ylaN, yloQ, ylqF, ymdA, yneS, yphC, yqeH, yqeI, yqjK, yrvO, ysxC, ytaG, ywlC) (Kunst et al. 1997). Homologs of the proteins encoded by these genes can be found in the various strains sequenced thus far of another gram-positive bacterium, the human pathogen *Staphylococcus aureus*. Amongst them, the Gcp and YneS orthologs are predicted membrane proteins, while the rest are predicted cytoplasmic proteins. Nonetheless, Obg has been shown to be partially bound to membranes in *B. subtilis* (Kobayashi et al. 2001).

SUMMARY

The inventors have isolated certain polypeptides that are essential components for growth of the pathogens *Bacillus subtilis* and *Staphylococcus aureus* and have raised antisera against these polypeptides. Antisera raised against the *Bacillus subtilis* polypeptides was found to result in extremely potent killing of *Staphylococcus aureus*. This effect could not have been predicted. The present findings facilitate the development of vaccines, immunogenic compositions and antibody therapies that mitigate some of the problems of current therapies such as antibiotic resistance.

The present disclosure provides antigenic polypeptides that are essential for growth of the gram-positive bacteria *Bacillus subtilis* and *Staphylococcus aureus* and which are useful in the treatment or prevention of microbial infections.

According to a first aspect, there is provided an antigenic polypeptide, or part thereof, encoded by an isolated nucleic acid sequence selected from the group consisting of:

i) a nucleic acid sequence as shown in FIGS. 1 to 6 (SEQ ID NO: 1-7);
ii) a nucleic acid sequence as in (i) which encodes a polypeptide expressed by a pathogenic organism;
iii) a nucleic acid sequence which hybridizes to a sequence identified in (i) or (ii) above; and
iv) a nucleic acid sequence that is degenerate as a result of the genetic code to the nucleic acid sequence defined in (i), (ii) or (iii)

for use as a medicament.

In one aspect, the medicament is a vaccine or immunogenic composition.

The nucleic acid encoding an antigenic polypeptide of the first aspect of the disclosure may anneal under stringent hybridization conditions to a nucleic acid sequence shown in FIGS. 1 to 6 (SEQ ID NO: 1-7) or to its complementary strand. Stringent hybridization/washing conditions are well known in the art. For example, nucleic acid hybrids that are stable after washing in 0.1×SSC, 0.1% SDS at 60° C. It is well known in the art that optimal hybridization conditions can be calculated if the sequences of the nucleic acid is known. For example, hybridization conditions can be determined by the GC content of the nucleic acid subject to hybridization. Please see Sambrook et at (1989) Molecular Cloning; A Laboratory Approach. A common formula for calculating the stringency conditions required to achieve hybridization between nucleic acid molecules of a specified homology is:

$$T_m = 81.5° C. + 16.6 \text{ Log } [Na^+] + 0.41 [\% \, G+C] - 0.63 (\% \text{ formamide}).$$

The nucleic acid encoding the antigenic polypeptide of the first aspect of the invention may comprise a sequence set out in FIGS. 1 to 6 (SEQ ID NO: 1-7) or a sequence which is at least 60%, 65%, 70%, 75%, 80%, 85%, 90%, 95%, for example 98%, or 99%, identical to a nucleic acid sequence set out in FIGS. 1 to 6 (SEQ ID NO: 1-7) at the nucleic acid residue level.

"Identity", as known in the art, is the relationship between two or more polypeptide sequences or two or more polynucleotide sequences, as determined by comparing the sequences. In the art, identity also means the degree of sequence relatedness between polypeptide or polynucleotide sequences, as the case may be, as determined by the match between strings of such sequences. Identity can be readily calculated (*Computational Molecular Biology*, Lesk, A. M. ed., Oxford University Press, New York, 1988; *Biocomputing: Informatics and Genome Projects*, Smith, D. W., ed., Academic Press, New York, 1993; *Computer Analysis of Sequence Data*, Part I, Griffin, A. M., AND Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991). While there exist a number of methods to measure identity between two polynucleotide or two polypeptide sequences, the term is well-known to skilled artisans (*Sequence Analysis in Molecular Biology*, von Heinje, G., Academic Press, 1987; *Sequence Analysis Primer*, Gribskov, M. and Devereux, J., eds., M Stockton Press, New York, 1991; and Carillo, H., and Lipman, D., *SIAM J. Applied Math.*, 48: 1073 (1988). Methods commonly employed to determine identity between sequences include, but are not limited to those disclosed in Carillo, H., and Lipman, D., *SIAM J. Applied Math.*, 48: 1073 (1988). Preferred methods to determine identity are designed to give the largest match between the sequences tested. Methods to determine identity are codified in computer programs. Preferred computer program methods to determine identity between two sequences include, but are not limited to, GCG program package (Devereux, J., et al., *Nucleic Acids Research* 12(1): 387 (1984)), BLASTP, BLASTN, and FASTA (Atschul, S. F. et al., *J. Molec. Biol.* 215: 403 (1990)).

The nucleic acid encoding an antigenic polypeptide disclosed herein may comprise a fragment of a sequence according which is at least 30 bases long, for example, 40, 50, 60, 70, 80 or 90 bases in length.

The nucleic acid sequence encoding the antigenic polypeptide of the first aspect of the invention may be genomic DNA, cDNA or RNA, for example mRNA.

The antigenic polypeptide of the first aspect of the invention may be a cell membrane protein, for example an integral membrane protein or a cytoplasmic protein.

Preferably, the antigenic polypeptide of the first aspect of the invention is expressed by a pathogenic organism, for example, a bacterium, virus or yeast. Preferably the pathogenic organism is a bacterium. The bacterium may be a gram-positive or gram-negative bacterium, preferably a gram-positive bacterium. The bacterium may be selected from the group consisting of: *Bacillus subtillis, Staphylococcus aureus; Staphylococcus epidermidis; Enterococcus faecalis; Mycobacterium tuberculsis; Streptococcus group B; Streptoccocus pneumoniae; Helicobacter pylori; Neisseria gonorrhea; Streptococcus group A; Borrelia burgdorferi; Coccidiodes immitis; Histoplasma sapsulatum; Neisseria meningitidis type B; Shigella flexneri; Escherichia coli; Haemophilus influenzae; Listeria monocytogenes, Bacillus anthracis, Corynebacterium diptheriae, Clostridium tetani, Mycoplasma spp.* and *Treponema pallidum*. Preferably the bacterium is of the genus *Staphylococcus* spp. Preferably still the bacterium is *Staphylococcus aureus*.

In a preferred embodiment of the invention, the antigenic polypeptide is associated with infective pathogenicity of an organism as defined herein.

In a further preferred aspect of the invention the antigenic polypeptide comprises all, or part of, an amino acid sequence shown in FIGS. 7 to 12 (SEQ ID NO: 8-14). As used herein "part of" may include a polypeptide fragment which may be at least 10, 15, 20 or 30 amino acids long. The antigenic polypeptide may comprise a non-protein antigen, for example a polysaccharide antigen.

As used herein, the term "polypeptide" means, in general terms, a plurality of amino acid residues joined together by peptide bonds. It is used interchangeably and means the same as peptide, protein, oligopeptide, or oligomer. The term "polypeptide" is also intended to include fragments, analogues and derivatives of a polypeptide wherein the fragment, analogue or derivative retains essentially the same biological activity or function as a reference protein.

According to a second aspect of the invention there is provided a vector comprising a nucleic acid sequence encoding a polypeptide disclosed herein.

The vector of the second aspect of the invention may be a plasmid, cosmid or phage. The vector may include a transcription control sequence (promoter sequence) which mediates cell specific expression, for example, a cell specific, inducible or constitutive promoter sequence. The vector may be an expression vector adapted for prokaryotic or eukaryotic gene expression, for example, the vector may include one or more selectable markers and/or autonomous replication sequences which facilitate the maintenance of the vector in either a eukaryotic cell or prokaryotic host (Sambrook et al. (1989) Molecular Cloning: A Laboratory Manual, Cold Spring Harbor Laboratory, Cold Spring Harbor, N.Y. and references therein; Marston, F (1987) DNA Cloning Techniques: A Practical Approach Vol III IRL Press, Oxford UK; DNA Cloning: F M Ausubel et al, Current Protocols in Molecular Biology, John Wiley & Sons, Inc. (1994). Vectors which are maintained autonomously are referred to as episomal vectors.

Promoter is an art recognized term and may include enhancer elements which are cis acting nucleic acid sequences often found 5' to the transcription initiation site of a gene (enhancers can also be found 3' to a gene sequence or even located in intronic sequences and is therefore position independent). Enhancer activity is responsive to trans acting transcription factors (polypeptides) which have been shown to bind specifically to enhancer elements. The binding/activity of transcription factors (see Eukaryotic Transcription Factors, by David S Latchman, Academic Press Ltd, San Diego) is responsive to a number of environmental cues which include intermediary metabolites (eg glucose, lipids), environmental effectors (e.g. light, heat).

Promoter elements also include so called TATA box and RNA polymerase initiation selection (RIS) sequences which function to select a site of transcription initiation. These sequences also bind polypeptides which function, inter alia, to facilitate transcription initiation selection by RNA polymerase.

The vector of the second aspect of the invention may include a transcription termination or polyadenylation sequences. This may also include an internal ribosome entry sites (IRES). The vector may include a nucleic acid sequence that is arranged in a bicistronic or multi-cistronic expression cassette.

According to a third aspect of the invention there is provided a method for the production of a recombinant antigenic polypeptide disclosed herein comprising:
(i) providing a cell transformed/transfected with a vector according to the second aspect of the invention;
(ii) growing said cell in conditions suitable for the production of said polypeptides; and
(iii) purifying said polypeptide from said cell, or its growth environment.

In a preferred aspect of the method of the third aspect, the vector encodes, and thus said recombinant polypeptide is provided with, a secretion signal to facilitate purification of said polypeptide.

According to a fourth aspect of the invention there is provided a cell or cell-line transformed or transfected with the vector according to the second aspect of the invention. In a preferred embodiment, said cell is a prokaryotic cell, for example, yeast or a bacterium such as *E. coli*. Alternatively said cell is a eukaryotic cell, for example a fungal, insect, amphibian, mammalian, for example, COS, CHO cells, Bowes Melanoma and other suitable human cells, or plant cell.

According to a fifth aspect of the invention there is provided a vaccine or immunogenic composition comprising at least one antigenic polypeptide, or part thereof, according to the first aspect of the invention. Preferably said vaccine or immunogenic composition further comprises a carrier and/or adjuvant. As used herein "part thereof" may include a fragment or subunit of the antigenic polypeptide wherein the fragment or subunit is sufficient to induce an antigenic response in a recipient.

The vaccine or immunogenic composition according to the fifth aspect may be a subunit vaccine or immunogenic composition in which the immunogenic part of the vaccine or immunogenic composition is a fragment or subunit of the antigenic polypeptide according to the first aspect of the invention.

The terms adjuvant and carrier are construed in the following manner. Some polypeptide or peptide antigens contain B-cell epitopes but no T cell epitopes. Immune responses can be greatly enhanced by the inclusion of a T cell epitope in the polypeptide/peptide or by the conjugation of the polypeptide/peptide to an immunogenic carrier protein such as key hole limpet haemocyanin or tetanus toxoid which contain multiple T cell epitopes. The conjugate is taken up by antigen presenting cells, processed and presented by human leukocyte antigens (HLA's) class II molecules. This allows T cell help to be given by T cell's specific for carrier derived epitopes to the B cell which is specific for the original antigenic polypeptide/peptide. This can lead to increase in antibody production, secretion and isotype switching.

An adjuvant is a substance or procedure which augments specific immune responses to antigens by modulating the activity of immune cells. Examples of adjuvants include, by example only, agonistic antibodies to co-stimulatory molecules, Freunds adjuvant, muramyl dipeptides, liposomes. An adjuvant is therefore an immunomodulator. A carrier is an immunogenic molecule which, when bound to a second molecule augments immune responses to the latter.

In yet a further aspect of the invention there is provided a method to immunize an animal against a pathogenic microbe comprising administering to said animal at least one polypeptide, or part thereof, according to the first aspect of the invention. Preferably, the polypeptide is in the form of a vaccine or immunogenic composition according to the fifth aspect of the invention. In a preferred method of the invention the animal is human.

Preferably the antigenic polypeptide of the first aspect, or the vaccine or immunogenic composition of the fifth aspect, of the invention can be delivered by direct injection either intravenously, intramuscularly, subcutaneously. Further still, the vaccine or antigenic polypeptide, may be taken orally. The polypeptide or vaccine may be administered in a pharmaceutically acceptable carrier, such as the various aqueous and lipid media, such as sterile saline, utilized for preparing injectables to be administered intramuscularly and subcutaneously. Conventional suspending and dispersing agents can be employed. Other means of administration, such as implants, for example a sustained low dose releasing bio-observable pellet, will be apparent to the skilled artisan.

The vaccine may be against the bacterial species *Staphylococcus aureus S. epidermidis, Streptococcus pneumoniae, Streptococcus pyogenes, B. anthracis*, and/or *Listeria monocytogenes*.

It will also be apparent that vaccines or antigenic polypeptides are effective at preventing or alleviating conditions in animals other than humans, for example and not by way of limitation, family pets (e.g. domestic animals such as cats and dogs), livestock (e.g. cattle, sheep, pigs) and horses.

A further aspect of the invention provides a pharmaceutical composition comprising an effective amount of at least one of the polypeptides of the invention, or a vaccine or immunogenic composition of the invention. These polypeptides may also include a pharmaceutically acceptable carrier or diluent.

According to a further aspect of the invention there is provided an antibody, or at least an effective binding part thereof, which binds at least one antigenic polypeptide, or part thereof, according to the invention.

As antibodies can be modified in a number of ways, the term "antibody" should be construed as covering any binding member or substance having a binding domain with the required specificity for the antigenic polypeptide. Thus, this term covers antibody fragments, derivatives, functional equivalents and homologues of antibodies, including any polypeptide comprising an immunoglobulin binding domain, whether natural or wholly or partially synthetic. Chimeric molecules comprising an immunoglobulin binding domain, or equivalent, fused to another polypeptide are therefore included. Cloning and expression of chimeric antibodies are described in EP-A-0120694 and EP-A-0125023.

In a preferred aspect of the invention said antibody is a polyclonal or monoclonal antibody.

In a further preferred aspect of the invention said antibody is a chimeric antibody produced by recombinant methods to contain the variable region of said antibody with an invariant or constant region of a human antibody.

In a further preferred aspect of the invention, said antibody is humanized by recombinant methods to combine the complementarity determining regions of said antibody with both the constant (C) regions and the framework regions from the variable (V) regions of a human antibody.

Preferably said antibody is provided with a marker including a conventional label or tag, for example a radioactive and/or fluorescent and/or epitope label or tag.

Preferably said humanized monoclonal antibody to said polypeptide is produced as a fusion polypeptide in an expression vector suitably adapted for transfection or transformation of prokaryotic or eukaryotic cells.

Antibodies, also known as immunoglobulins, are protein molecules which have specificity for foreign molecules (antigens). Immunoglobulins (Ig) are a class of structurally related proteins consisting of two pairs of polypeptide chains, one pair of light (L) (low molecular weight) chain ($\kappa$ or $\lambda$), and one pair of heavy (H) chains ($\gamma$, $\alpha$, $\mu$, $\delta$ and $\epsilon$), all four linked together by disulphide bonds. Both H and L chains have regions that contribute to the binding of antigen and that are highly variable from one Ig molecule to another. In addition, H and L chains contain regions that are non-variable or constant.

The L chains consist of two domains. The carboxy-terminal domain is essentially identical among L chains of a given type and is referred to as the "constant" (C) region. The amino terminal domain varies from L chain to L chain and contributes to the binding site of the antibody. Because of its variability, it is referred to as the "variable" (V) region.

The H chains of Ig molecules are of several classes, $\alpha$, $\mu$, $\sigma$, $\alpha$, and $\gamma$ (of which there are several sub-classes). An assembled Ig molecule consisting of one or more units of two identical H and L chains, derives its name from the H chain that it possesses. Thus, there are five Ig isotypes: IgA, IgM, IgD, IgE and IgG (with four sub-classes based on the differences in the H chains, i.e., IgG1, IgG2, IgG3 and IgG4). Further detail regarding antibody structure and their various functions can be found in, Using Antibodies: A Laboratory Manual, Cold Spring Harbor Laboratory Press.

Chimeric antibodies are recombinant antibodies in which all of the V-regions of a mouse or rat antibody are combined with human antibody C-regions. Humanized antibodies are recombinant hybrid antibodies which fuse the complementarity determining regions from a rodent antibody V-region with the framework regions from the human antibody V-regions. The C-regions from the human antibody are also used. The complementarity determining regions (CDRs) are the regions within the N-terminal domain of both the heavy and light chain of the antibody to where the majority of the variation of the V-region is restricted. These regions form loops at the surface of the antibody molecule. These loops provide the binding surface between the antibody and antigen.

Antibodies from non-human animals provoke an immune response to the foreign antibody and its removal from the circulation. Both chimeric and humanized antibodies have reduced antigenicity when injected to a human subject because there is a reduced amount of rodent (i.e. foreign) antibody within the recombinant hybrid antibody, while the human antibody regions do not illicit an immune response. This results in a weaker immune response and a decrease in the clearance of the antibody. This is clearly desirable when using therapeutic antibodies in the treatment of human diseases. Humanized antibodies are designed to have less "foreign" antibody regions and are therefore thought to be less immunogenic than chimeric antibodies.

In a further preferred embodiment of the invention said antibodies are antibodies whose activity is mediated by complement, for example the activity of the antibody may be activated by complement.

In another aspect of the invention there is provided a vector comprising a nucleic acid sequence encoding the humanized or chimeric antibodies according to the invention.

In a yet further aspect of the invention, there is provided a cell or cell line which comprises the vector encoding the humanized or chimeric antibody according to the invention. The cell or cell line may be transformed or transfected with the vector encoding the humanized or chimeric antibody according to the invention.

In a yet further aspect of the invention there is provided a hybridoma cell line which produces a monoclonal antibody as hereinbefore described.

In a further aspect of the invention there is provided a method of producing monoclonal antibodies according to the invention using hybridoma cell lines according to the invention.

In a yet further aspect of the invention there is provided a method for the production of the humanized or chimeric antibody according to the invention comprising:
(i) providing a cell transformed or transfected with a vector which comprises a nucleic acid molecule encoding the humanized or chimeric antibody according to the invention;
(ii) growing said cell in conditions suitable for the production of said antibody; and
(iii) purifying said antibody from said cell, or its growth environment.

In a further aspect of the invention there is provided a method for preparing a hybridoma cell-line according to the invention comprising the steps of:
i) immunizing an immunocompetent mammal with an immunogen comprising at least one polypeptide having an amino acid sequence as represented in FIGS. 7 to 12 (SEQ ID NO: 8-14), or fragments thereof;
ii) fusing lymphocytes of the immunized immunocompetent mammal with myeloma cells to form hybridoma cells;
iii) screening monoclonal antibodies produced by the hybridoma cells of step (ii) for binding activity to the amino acid sequences of (i);
iv) culturing the hybridoma cells to proliferate and/or to secrete said monoclonal antibody; and
v) recovering the monoclonal antibody from the culture supernatant.

The immunocompetent mammal may be a mouse, rat or rabbit.

The production of monoclonal antibodies using hybridoma cells is well-known in the art. The methods used to produce monoclonal antibodies are disclosed by Kohler and Milstein in Nature 256, 495-497 (1975) and also by Donillard and Hoffman, "Basic Facts about Hybridomas" in Compendium of Immunology V.II ed. by Schwartz, 1981, which are incorporated by reference.

In a further aspect of the invention there is provided the use of an antigenic polypeptide according to the first aspect of the invention in the manufacture of a medicament for the treatment or prophylaxis of a microbial infection or a microbe related disorder.

Preferably, the microbial infection is a bacterial infection caused by a bacterial pathogen derived from a bacterial species selected from the group consisting of: *Staphylococcus* spp e.g. *Staphylococcus aureus, Staphylococcus pyrogenes, Staphylococcus epidermidis; Enterococcus* spp e.g. *Enterococcus faecalis; Lysteria* spp; *Pseudomonas* spp; *Mycobacterium* spp e.g. *Mycobacterium tuberculsis; Enterobacter* spp; *Campylobacter* spp; *Salmonella* spp; *Streptococcus* spp, e.g. *Streptococcus* group A or B, *Streptoccocus pneumoniae; Helicobacter* spp, e.g. *Helicobacter pylori; Neisseria* spp e.g. *Neisseria gonorrhea, Neisseria meningitidis; Borrelia burgdorferi* spp; *Shigella* spp, e.g. *Shigella flexneri; Escherichia coli* spp; *Haemophilus* spp, e.g. *Haemophilus influenza; Chlamydia* spp e.g. *Chlamydia trachomatis, Chlamydia pneumoniae, Chlamydia psittaci; Francisella tularensis; Bacillus* spp, e.g. *Bacillus anthracis; Clostridia* spp, e.g. *Clostridium botulinum; Yersinia* spp, e.g. *Yersinia pestis; Treponema* spp; and *Burkholderia* spp, e.g. *Burkholderia mallei* and *B pseudomallei*.

The bacteria related disorder may be a *Staphylococcus aureus*-associated disorder. A *Staphylococcus aureus*-associated disorder may include, for example, septicaemia; tuberculosis; bacteria-associated food poisoning; blood infections; peritonitis; endocarditis; osteomyelitis; sepsis; skin disorders, meningitis; pneumonia; stomach ulcers; gonorrhoea; strep throat; streptococcal-associated toxic shock; necrotizing fasciitis; impetigo; histoplasmosis; Lyme disease; gastroenteritis; dysentery; and shigellosis In a further aspect of the invention there is provided the use of antibodies according to the invention in the manufacture of a medicament for the treatment of a microbial infection.

In a further aspect of the invention there is provided a method of treating a patient comprising administering to the patient an antigenic polypeptide according to the first aspect of the invention, or a vaccine or immunogenic composition according to the fifth aspect of the invention, or an antibody according to the invention.

Throughout the description and claims of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

An embodiment of the invention will now be described by example only and with reference to the following materials, methods and figures.

BRIEF DESCRIPTION OF THE DRAWINGS

FIG. 1 shows the DNA sequence of the yphC polypeptide from Bacillus subtilis (SEQ ID NO: 1);

FIG. 2 shows the DNA sequence of the ysxC polypeptide from Bacillus subtilis (SEQ ID NO: 2);

FIG. 3 shows the DNA sequence of the ywlC polypeptide from Bacillus subtilis (SEQ ID NO: 3);

FIG. 4 shows the DNA sequence of the yneS ortholog peptide 731 from Staphylococcus aureus (SEQ ID NO: 4);

FIG. 5 shows the DNA sequence of the yneS ortholog peptide 733 from Staphylococcus aureus (SEQ ID NO: 5);

FIG. 6 shows (a) the DNA sequence encoding the gcp region putatively exposed outside of the membrane (SEQ ID NO: 6); and (b) the full DNA sequence of the gcp ortholog polypeptide, both from Staphylococcus aureus (SEQ ID NO: 7);

FIGS. 7 to 11 show the amino acid sequences (SEQ ID NO: 8-12) corresponding to the DNA sequences shown in FIGS. 1 to 5 (SEQ ID NO: 1-5) respectively;

FIGS. 12(a) and (b) show the amino acid sequences (SEQ ID NO: 13 and 14) corresponding to the DNA sequences shown in FIGS. 6(a) and (b) (SEQ ID NO: 6 and 7) respectively;

DETAILED DESCRIPTION

Materials and Methods

Strains

Figure 13:
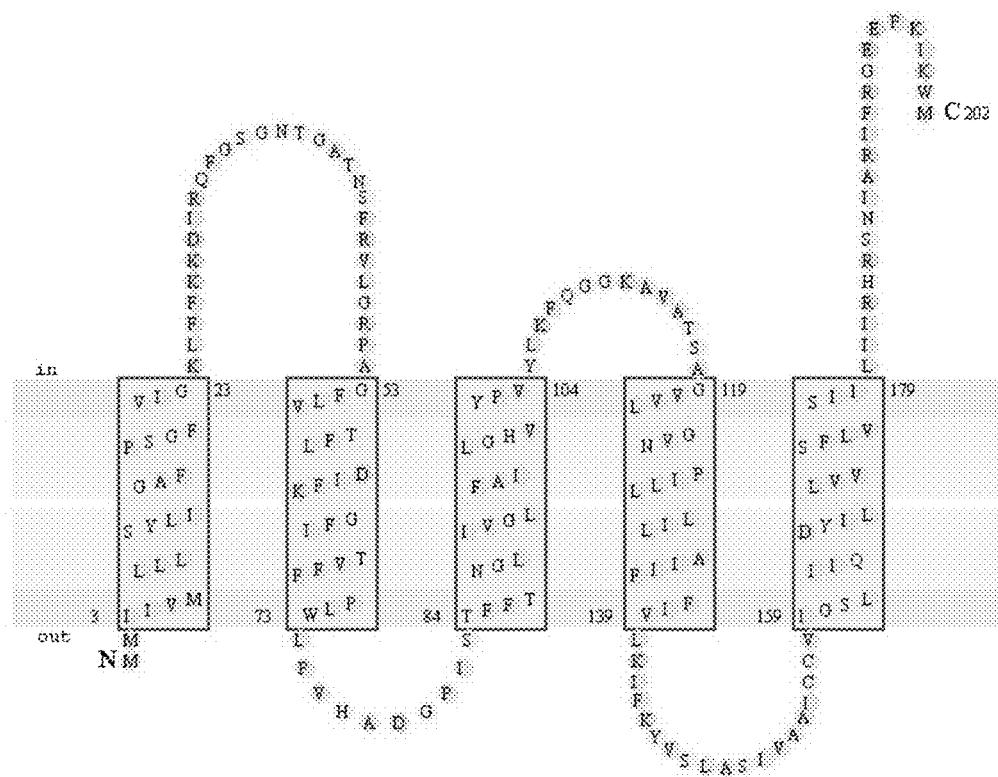
FIGS. 13 and 14 show hydropathy plots of the membrane proteins yneS and gcp. The calculation of the hydropathy plots of the proteins stated above and the corresponding graphic representation to predict the transmembrane topology model was determined according to the ConPredII Method and was carried in the server http://bioinfo.si.hirosaki-u.ac.jp/~ConPred2/.
Figure 14:
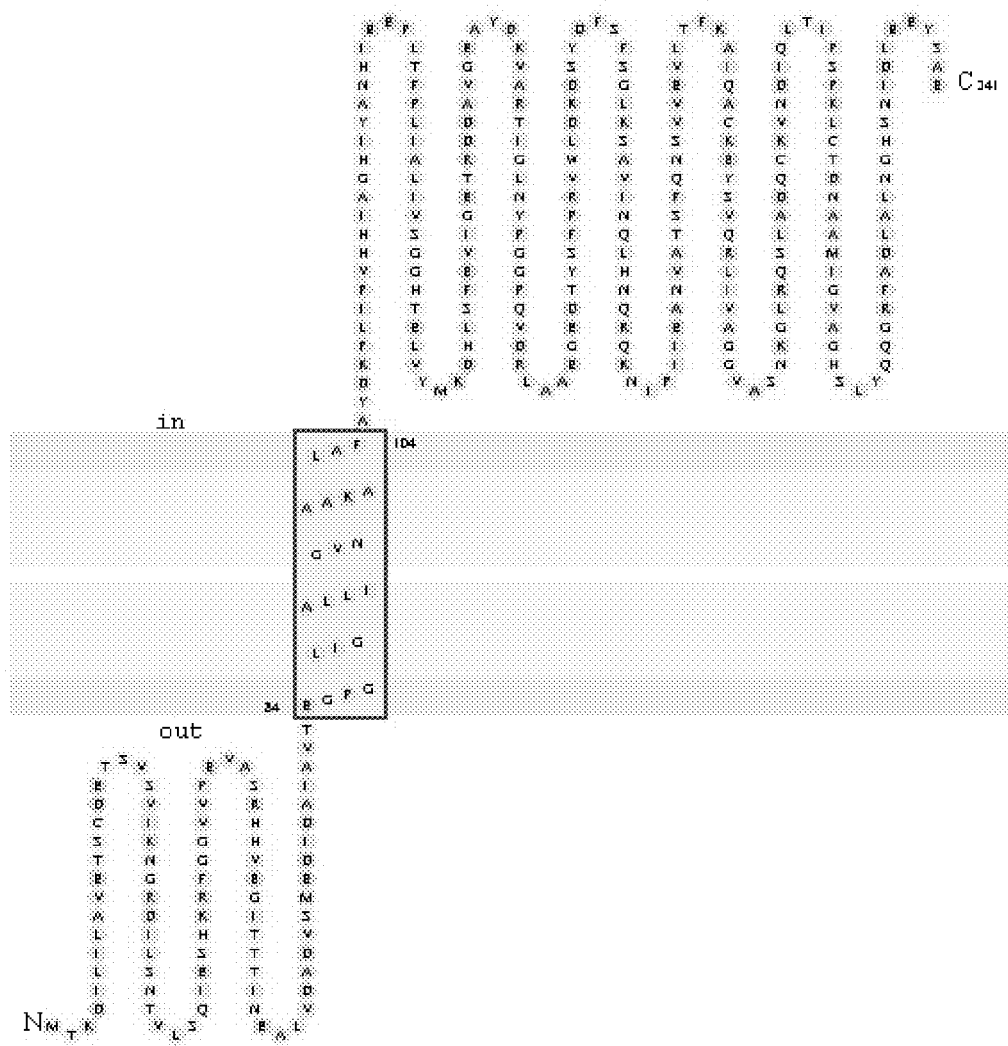

The chromosomal DNA used for PCR amplification of the gene sequences of interest were B. subtilis subsp. subtilis str. 168, S. aureus NCTC 8325, S. aureus N315 and S. aureus COL. An erythromycin resistant sodA::lacZ transcriptional fusion derivative of S. aureus SH1000 (S. aureus SJF741), was the strain used in the assays (Horsburgh et al. 2002).

DNA, Protein and Peptide Sequences Used as Antigens.

The gene and protein sequences of the genes mentioned can be found at:

B. subtilis subsp. subtilis str. 168: GenBank Accession AL009126;

S. aureus 8325 (this is a non-annotated sequence; equivalent annotated sequences of S. aureus containing the genes of interest can be found below): Iandolo et al., 2002; Novick, 1967;

Other S. aureus Strains:

S. aureus subsp aureus str. N315: Kuroda, 2001;

S. aureus strain subsp. aureus COL: The Center for Genomic Research; NCBI Taxonomy Database, Taxonomy ID 93062

NOTE: Different strains of S. aureus have different locus names for the same genes due to phage insertions within the sequence. In this document, the locus names used for the S. aureus genes correspond to those in the S. aureus N315 sequence.

Antigen Preparation

The genes encoding selected proteins from Bacillus subtilis 168 (Obg, YdiB, YphC (FIG. 1; SEQ ID NO: 1), YsxC (FIG. 2; SEQ ID NO: 2), YwlC (FIG. 3; SEQ ID NO: 3), and S. aureus N315 (SA1387, Gcp/SA1854 (FIG. 6; SEQ ID NO: 6 and 7)) were amplified by PCR. The resulting products were cloned in plasmid pETBlue-1, and the genes overexpressed in Escherichia coli Tuner™(DE3) pLacI Competent Cells (Novagen) according to the manufacturer's instructions. The overexpressed proteins were purified in a 3-step scheme based on anion exchange, hydrophobic and gel filtration chromatography. The level of protein overexpression was confirmed by SDS-PAGE, and the purity had an average of 90%. In addition, selected peptides within the S. aureus N315 protein SA1187 (YneS-731 (FIG. 4; SEQ ID NO: 4) and YneS-733 (FIG. 5; SEQ ID NO: 5)) were synthesized on a Milligen 9050 Peptide Synthesizer using F-moc chemistry. The F-moc amino acids (Novobiochem/Merck) were activated immediately before coupling using equimolar amounts of HCTU or HBTU in the presence of a 10% molar excess of HOBt. In both cases, a cysteine was incorporated at the C-terminus of the peptide to enable linkage to carrier protein by assembling the peptide on Fmoc-L-Cys(Trt)-PEG-PS resin (Applied Biosystems). Peptides were purified using a C18 Vydac column (22×250 mm) using gradients of acetonitrile in 0.1% TFA. Peptides were verified by mass spectrometry. The purified peptides were conjugated to KLH (Sigma) (carrier protein) to enhance immunogenicity of the hapten in the rabbit. Conjugation was performed in 10×PBS using MBS (Sigma).

Sera

Sera were obtained from the Antibody Resource Center at the University of Sheffield from: i) rabbits immunized against proteins from *B. subtilis* (Obg, YdiB, YphC, YwlC and YsxC and *S. aureus* (Gcp, SA1387); ii) rabbits immunized against KLH-conjugated peptides selected within the *S. aureus* protein SA1187 (YneS-731, YneS-733); iii) rabbits immunized against a KLH-conjugated peptide from the cyclophilin protein from *Arabidopsis thaliana*; iv) naive (non-immune) rabbit serum; and v) human serum from a patient convalescent from a *S. aureus* infection.

The immunization process was performed as follows. For each rabbit 200 to 500 µg of antigen (in a maximum volume of 250 ul of Phosphate Buffer Saline, PBS) were mixed with an equal volume of complete Freund's adjuvant. The solution was filtered through a 23G needle until an emulsion formed which did not separate on standing. Each rabbit was inoculated with a maximum of 500 µl subcutaneously. On day 22, 43 and 64 the injection was repeated but using incomplete Freund's adjuvant. Sample bleeds were collected on day 53 and after day 64. Injection dates were flexible within a range of 3 to 6 weeks. When a suitable titer was detected in the test serum, a final boost followed by bleed out 10 days later was performed.

Sera were stored frozen being thawed and filtered through 0.2 µm pore diameter filters (Minisart High Flow, Sartorius) immediately before use in killing experiments.

Using western blot analysis (data not shown) it was shown that antibodies against the *B. subtilis* YdiB recognize a band of the size corresponding to the YdiB homolog in *S. aureus*, suggesting the species cross-reactivity of these antibodies.

Media and Growth Conditions

To prepare the inoculum for the serum experiments, *S. aureus* SJF741 was grown at 37° C. in Brain Heart Infusion medium (BHI; Oxoid) supplemented with erythromycin (Sigma) to a final concentration of 5 µg/ml (BHI-Ery).

Preparation of the Inoculum

A single colony of *S. aureus* SJF741 freshly grown on BHI-Ery plates from the laboratory frozen stock was inoculated in 30 ml universals containing 5 ml of BHI-Ery and incubated overnight (between 12 to 16 hours) at 37° C. in an orbital shaker (250 rpm). A 10-fold dilution in Phosphate Saline Buffer (PBS) of the resulting culture was prepared immediately before inoculation into serum.

Serum Experiments

Aliquots of 200 µl from the various sera in 1.5 ml microfuge tubes were inoculated with the PBS dilution of *S. aureus* SJF741 (See Preparation of the inoculum) to a final cell density of $1\times10^6$ to $1\times10^7$ cells/ml, followed by incubation in a rotary shaker at 37° C. 10 ul samples were taken periodically from these serum cultures, serially diluted, and 10 ul from each dilution plated on BHI-Ery plates, which were subsequently incubated at 37° C. overnight. In addition, another 10 ul sample from each serum culture was directly plated on BHI-Ery plates. Only the dilutions rendering between 1 to 40 colonies were enumerated and the number of viable cells (colony forming units, CFU) per ml determined.

Results

Figure 15:
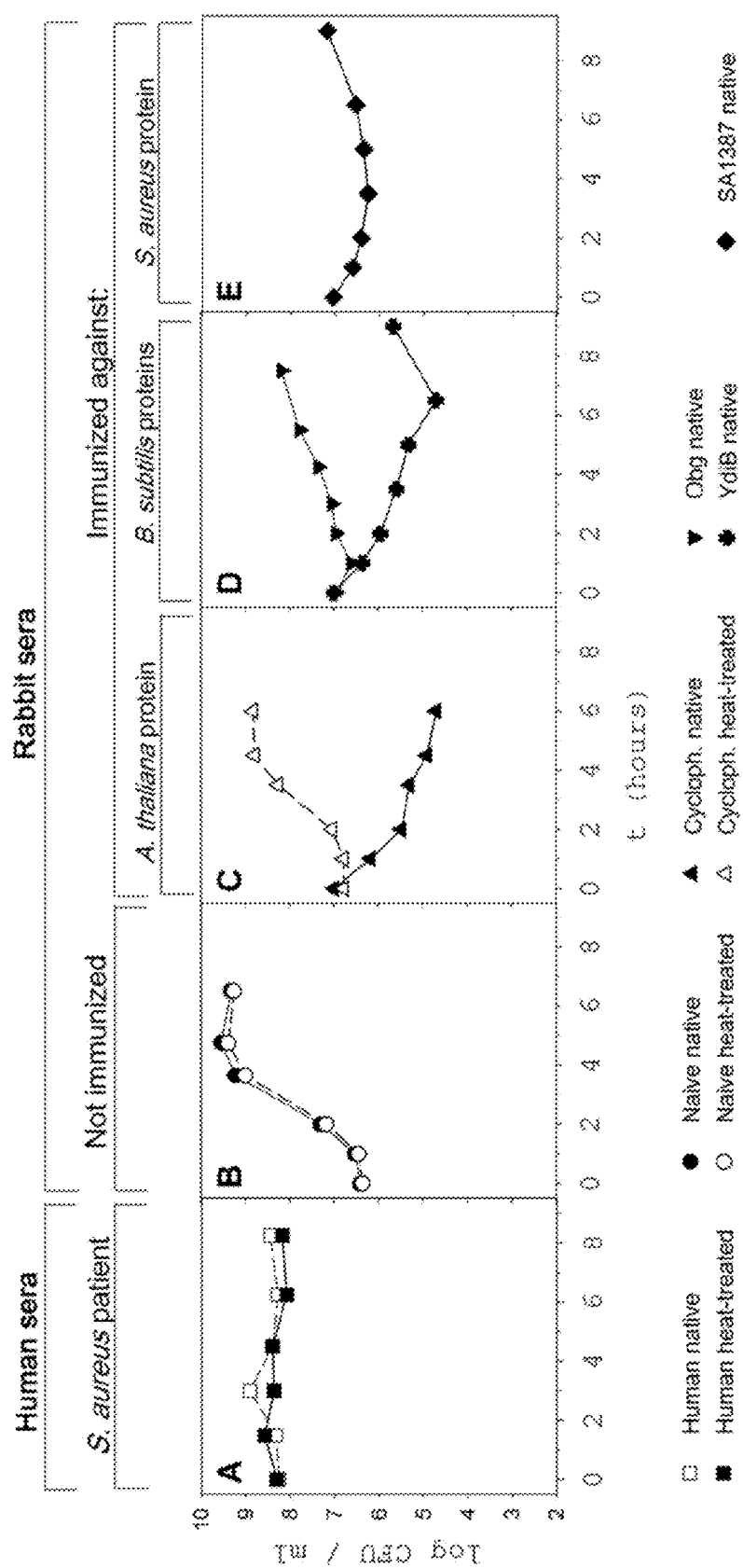
FIG. 15 shows graphs showing that heat treatment of sera from a human patient (□), from a non-immunized rabbit (○) or from sera raised against the A. thaliana cyclophilin protein (Δ) did not induce death of S. aureus SJF741. No killing of S. aureus SJF741 was observed either when using native sera from a patient convalescent from S. aureus infection (■) (Panel A) and from a non-immunized rabbit (●) (Panel B). When native sera raised against the A. thaliana cyclophilin protein (▲) (Panel C), against the B. subtilis proteins Obg (▼) and YdiB (✦) (Panel D) and against the S. aureus protein SA1387 (♦) (Panel E) a minor decrease in the number of S. aureus SJF741 during the first 6 hours was observed, which was followed by subsequent recovery.

To evaluate the staphylococcal killing abilities of the various sera, *S. aureus* was challenged with the various rabbit anti-sera and survival over time was evaluated. The results showed that *S. aureus* was dramatically killed within 2 to 3 hours of contact with sera (FIG. 16) containing antibodies against Gcp and YneS, as well as to other surface proteins. In contrast, antibodies against cytoplasmic proteins from *B. subtilis* (Obg and YdiB), to a membrane protein from *Arabidopsis thaliana* (cyclophilin), and to various normal rabbit sera did not show the bactericidal phenotype (FIG. 15). Strikingly, sera from rabbits immunized against other presumed cytoplasmic proteins from *B. subtilis* (YsxC and YphC and YwlC) also revealed a killing phenotype similar to the one observed for Gcp and YneS (731 and 733) antibodies. This was unexpected since YsxC, YphC and YwlC are presumed cytoplasmic proteins and, therefore, are not surface exposed and so the antisera would not be expected to recognize them.

Figure 16:
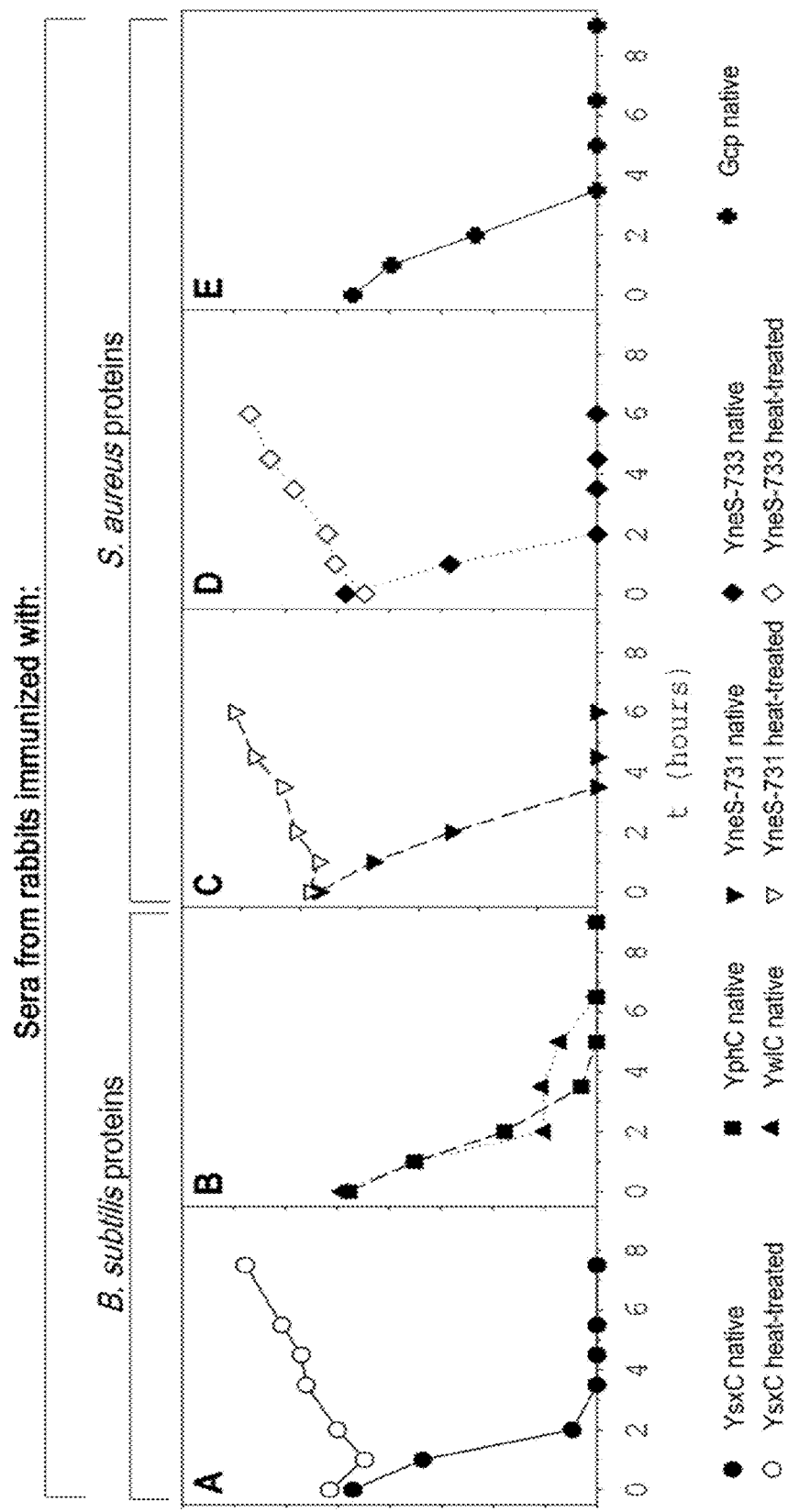
FIG. 16 shows graphs showing that native sera raised against the B. subtilis proteins YsxC (●), YphC (■), and YwlC (▲) (Panels A and B) killed S. aureus SJF471 dramatically, a 5 log decrease within 2 to 4 hours. A similar effect was observed when using native sera raised against the S. aureus peptides YneS-731 (▼) and YneS 733 (♦) and the S. aureus protein Gcp (✦) (Panels C-E). In contrast, heat treating the sera raised against the B. subtilis YsxC protein (○) or the S. aureus peptides YneS-731 (▽) and YneS-733 (◇) (Panels A, C, D) abolished the killing abilities of these sera, which were able to kill S. aureus SJF741 in the native form (not heat-treated), as indicated above. Hence, the killing abilities of the sera are due to a heat labile component, which is inactivated in the heat treated sample. No experiments using heat treated sera raised against the B. subtilis proteins YphC (■) and YwlC (▲) or against the S. aureus gcp protein (✦) are shown in this figure, and the experiments with the corresponding native sera (Panels B and E), as indicated above, illustrate the S. aureus killing capability of these sera.

This work suggests the location of YsxC in the membrane fraction of *S. aureus*. This work has further demonstrated that the killing effect is mediated through a heat-labile component (inactivated by heat treatment, See Material and Methods) present in serum, likely to correspond to some of the components of the complement (FIG. 16).

REFERENCES

Horsburgh et al., J. Bacteriol. 184(9):5457-67 (2002)
Iandolo et al., Gene 289 109-118 (2002).
Ikeda et al., *In Silico Biol.*, 2, 19-33 (2002).
Ikeda et al., Nucleic Acids Res., 31, 406-409 (2003).
Karavolos et al., Microbiology October; 149(Pt 10):2749-58 (2003).
Kobayashi et al., Mol Microbiol. September; 41(5):1037-51 (2001).
Kobayashi et al. Proc Natl Acad Sci USA 100(8):4678-83 (2003).
Kunst et al., Nature, November 20; 390(6657):249-56 (1997).
Kuroda et al. Lancet, 357:1225-1240 (2001).
Lao and Shimizu In Valafar, F. (ed.), *Proceedings of the 2001 International Conference on Mathematics and Engineering Techniques in Medicine and Biological Sciences (MET-MBS '01)*, CSREA Press, USA, pp. 119-125 (2001).
Lao et al., Bioinformatics, 18, 562-566 (2002).
Lao et al., *In Silico Biol.*, 2, 485-494 (2002).
Moszer et al., Nucleic Acids Res. 30(1):62-5 (2002).
Novick, R. P. Virology 33:155-156 (1967).
Xia et al., *Comput. Biol. Chem.*, 28, 51-60 (2004).
Zalacain et al. J Mol Microbiol Biotechnol. 6(2):109-26 (2003).

We claim:

1. An isolated antibody, or at least an effective binding part thereof, which binds to an isolated antigenic peptide encoded by an isolated nucleic acid sequence consisting of:
   SEQ ID NO: 5.

2. The antibody of claim 1, wherein the antibody is a polyclonal or monoclonal antibody.

3. The antibody of claim 1, wherein the antibody is a chimeric antibody produced by recombinant methods to contain the variable region of said antibody with an invariant or constant region of a human antibody.

4. the antibody of claim 1, wherein the antibody is humanized by recombinant methods to combine the complementarity determining regions of said antibody with both the constant (C) regions and the framework regions from the variable (V) regions of a human antibody.

5. A method for preparing a hybridoma cell-line comprising the steps of:
   i) immunizing an immunocompetent mammal with a peptide consisting of an amino acid sequence SEQ ID NO: 12;
   ii) fusing lymphocytes of the immunized immunocompetent mammal with myeloma cells to form hybridoma cells;
   iii) screening monoclonal antibodies produced by the hybridoma cells of step (ii) for binding activity to the amino acid sequence of (i);
   iv) culturing the hybridoma cells to proliferate and/or to secrete said monoclonal antibody; and
   v) recovering the monoclonal antibody from the culture supernatant.

6. An isolated antibody, or at least an effective binding part thereof, which binds to an isolated antigenic peptide consisting of SEQ ID NO: 12.

7. The antibody of claim 6, wherein the antibody is a polyclonal or monoclonal antibody.

8. The antibody of claim 6, wherein the antibody is a chimeric antibody produced by recombinant methods to contain the variable region of said antibody with an invariant or constant region of a human antibody.

9. The antibody of claim 6, wherein the antibody is humanized by recombinant methods to combine the complementarity determining regions of said antibody with both the constant (C) regions and the framework regions from the variable (V) regions of a human antibody.

* * * * *

SEQUENCE LISTING

<160> NUMBER OF SEQ ID NOS: 16

<210> SEQ ID NO 1
<211> LENGTH: 1308
<212> TYPE: DNA
<213> ORGANISM: Bacillus subtilis

<400> SEQUENCE: 1
atgggtaaac ctgtcgtagc cattgtcggg agaccaaatg taggaaaatc cacaatcttt    60

```
aaccggattg cgggagaaag aatttcaata gtagaagata cccctggcgt gacaagggat    120
cggatataca gctcggctga atggctgaat tatgatttta atttgattga tacgggcggt    180
attgatatcg gtgatgagcc gttttttagcg cagattcgcc agcaagctga atcgccatg    240 gatgaagcgg acgtgattat ttttatggtg aacggccgtg aaggcgtgac agctgctgat    300
gaagaagtgg cgaaaatttt gtaccgcaca aaaaagcctg ttgttttagc ggttaataaa    360
ctggataaca cagaaatgag agcgaatatt tatgattttt attcgctagg ctttggcgag    420
ccgtatccaa tttcgggaac acacggactc ggactgggtg atttactgga tgccgttgca    480
gagcatttta aaaacattcc tgaaacgaaa tacaatgaag aagttattca attctgtctg    540
atcggacgtc caaatgtcgg aaagtcttca cttgtgaatg cgatgctcgg cgaagaacgc    600
gttattgtca gcaacgtggc tggaacgaca agagatgctg ttgatacgtc atttacttac    660
aaccagcagg agtttgtcat tgtcgatact gcaggtatgc gaaaaaaagg gaaagtctat    720
gaaacgactg agaagtatag tgtactgcgg gcgctaaaag cgattgaccg ctcagaagtc    780
gtggcggttg tgctggatgg cgaagaaggc attattgaac aggacaagcg tatcgccggt    840
tatgcacacg aagcgggcaa ggccgtcgtc atcgtcgtaa acaaatggga tgctgttgac    900
aaagatgaga gcacgatgaa agaatttgaa gaaaatattc gcgatcattt tcaatttctg    960
gattatgcgc caatcctatt tatgtctgcc ttaacgaaaa aacggatcca tactctgatg   1020
cctgcgatta tcaaagctag tgaaaatcat tcacttcgag ttcaaacaaa cgtcttaaat   1080
gatgtcatca tggacgctgt ggcaatgaat ccgacaccga ctcataacgg ttctcgtttg   1140
aaaatttact atgcgactca agtgtcggta aagccgccaa gcttcgttgt gtttgtaaac   1200
gatccggaac tgatgcattt ttcatacgaa cggttttttag aaaaccgaat cagagacgcg   1260
ttcggttttg aggggacacc aatcaaaata tttgcaagag ctagaaaa                1308

<210> SEQ ID NO 2
<211> LENGTH: 585
<212> TYPE: DNA
<213> ORGANISM: Bacillus subtilis

<400> SEQUENCE: 2
atgaaagtca caaagtcaga atcgtgatc agtgcagtaa aaccggaaca gtaccctgaa    60 gggggcttc cggaaatcgc attggccgga agatcgaacg taggaaaatc gtctttatc    120 aattcattaa tcaatcgcaa aaatcttgcg agaacgtcat caaagccggg aaaaacacaa    180
acgcttaatt tctacattat caatgatgag ctgcattttg tggatgtgcc gggctacggt    240
tttgccaaag tgtcaaagtc tgagcgtgaa gcatggggca gaatgattga aacctatatc    300
acgacacgcg aggaattaaa agctgtggt cagatcgttg atttgcggca tgcgccatct    360
aatgatgatg tacagatgta tgaattttta agtattacg gcattcctgt tattgttatc    420
gctacaaagg cggataagat cccgaaaggt aaatgggaca acacgcgaa ggttgtccga    480 caaacattaa atattgatcc ggaagacgag ctgatcctct tttcttcaga aacgaaaaag    540
ggaaaagacg aagcttgggg agcgatcaaa aaaatgataa accgg                  585

<210> SEQ ID NO 3
<211> LENGTH: 1038
<212> TYPE: DNA
<213> ORGANISM: Bacillus subtilis

<400> SEQUENCE: 3
atgaaaacga aagatggtt tgtggatgta actgacgagt tatccacaaa tgatccacaa    60
```

| | |
|---|---:|
| attgcacaag cagccgcttt gctccgagaa aatgaggtcg ttgcctttcc gacagaaaca | 120 |
| gtatatggcc taggcgcaaa cgcaaaaaat acggatgccg tcaaaaaaat atatgaggcg | 180 |
| aaagggcggc cgagcgataa tcccctgatt gtccacattg cggatatcag ccagcttgag | 240 |
| gatttaacgg gcccggcgcc ggaaaaggcg aaaacattga tgaaacggtt ttggccggga | 300 |
| gcacttacgc tcattctgcc ttgcaaacct gatgcgcttt cacctcgtgt aacggcaggt | 360 |
| cttgaaacgt tgccattag aatgccggat catccgcttg cccttgcatt gattcgcgaa | 420 |
| tcgggactgc cgattgcagc accgagcgcc aatctatcag gcaagccaag tcccacaaaa | 480 |
| gcggagcatg tggctcacga cttggatggc cgcatagccg gtattgtgga tggaggccct | 540 |
| accggaatcg gggtcgaatc aactgtgctt tcatgtgcgg acgacatccc tgttctcttg | 600 |
| cgtcctggcg gcattacgaa ggaacaaatt gaagcggtga tcgggccgat ccatgtggat | 660 |
| aaagggctca gcgaccaaaa cgagaagccg atttctccag ggatgaaata tacacattat | 720 |
| gcgccgacag cgcctcttgc catttgcgaa ggcagcccag agcgcattca gcacctcatt | 780 |
| caagaatatc aacagggtgg aagacgggtc ggtgtcctga cgacagaaga aaaagcgggc | 840 |
| gtttattccg ctgattatgt gaagagctgc ggaagacggg ctcagcttga gactgttgcg | 900 |
| gcagggctgt atgatgcttt gcgcagcttt gatgagaata aggtggattt cattatagcg | 960 |
| gaatcctttc cggatacagg tgtcggtctt gctattatga acaggctgat gaaagccgcc | 1020 |
| ggaggaagag tgattcgc | 1038 |

<210> SEQ ID NO 4
<211> LENGTH: 30
<212> TYPE: DNA
<213> ORGANISM: Staphylococcus aureus

<400> SEQUENCE: 4

| | |
|---|---:|
| ttaccagttc acgcagatgg ccctattagt | 30 |

<210> SEQ ID NO 5
<211> LENGTH: 30
<212> TYPE: DNA
<213> ORGANISM: Staphylococcus aureus

<400> SEQUENCE: 5

| | |
|---|---:|
| ttgaagattt ttaaatatgt ttctttagca | 30 |

<210> SEQ ID NO 6
<211> LENGTH: 249
<212> TYPE: DNA
<213> ORGANISM: Staphylococcus aureus

<400> SEQUENCE: 6

| | |
|---|---:|
| atgactaaag atatattaat actagctgtt gaaacaagtt gtgatgaaac aagcgttagt | 60 |
| gttataaaaa atggcagaga tattttatca aatacagttt taagtcagat tgaaagtcat | 120 |
| aaacgatttg gcggtgtcgt tcccgaagtg gcaagtagac atcacgttga aggtataaca | 180 |
| acaacaataa acgaggctct agtggatgcc gatgtatcaa tggaagatat tgatgccata | 240 |
| gcggttaca | 249 |

<210> SEQ ID NO 7
<211> LENGTH: 1026
<212> TYPE: DNA
<213> ORGANISM: Staphylococcus aureus

<400> SEQUENCE: 7

```
atgactaaag atatattaat actagctgtt gaaacaagtt gtgatgaaac aagcgttagt    60
gttataaaaa atggcagaga tatttatca aatacagttt taagtcagat tgaaagtcat   120
aaacgatttg gcggtgtcgt tcccgaagtg gcaagtagac atcacgttga aggtataaca   180
acaacaataa acgaggctct agtggatgcc gatgtatcaa tggaagatat tgatgccata   240
gcggttacag aaggccctgg actaattggt gcgttactaa taggtgttaa tgcagccaaa   300
gcattggcat ttgcttacga taagccactt attcctgttc atcatattgc aggacatata   360
tatgctaatc acatagaaga gccattaaca ttcccgctaa ttgcacttat tgtttcaggt   420
ggacatactg aattagttta tatgaaagat catttatcat ttgaagtcat tggtgaaaca   480
cgagatgacg cagtaggtga ggcttatgat aaagtggcac gaacaattgg tttaaattat   540
ccaggtggtc cacaagttga tcggttggct gctgaaggtg aagatactta ttcattccct   600
cgtgtttggt tggataaaga tagttatgat tttagtttta gtgggttgaa aagtgccgtg   660
atcaatcaac ttcacaatca acgacaaaaa aatattccaa tcattgaagc taacgtagca   720
acgagctttc aaaatagtgt tgtagaggtg cttacgttta aagctattca agcttgtaaa   780
gaatatagtg ttcagcgatt aattgttgct ggtggcgtgg cgagtaataa aggattacgt   840
caatctttag cggatcaatg caaagtcaat gacattcaat taactatccc aagtcctaaa   900
ttatgcacag ataatgctgc aatgataggc gttgccggcc actctttgta tcagcaaggt   960
cgatttgctg atttagcatt aaatgggcac agcaatatag atttagaaga gtattctgca  1020
gaataa                                                             1026
```

<210> SEQ ID NO 8
<211> LENGTH: 436
<212> TYPE: PRT
<213> ORGANISM: Bacillus subtilis

<400> SEQUENCE: 8

```
Met Gly Lys Pro Val Val Ala Ile Val Gly Arg Pro Asn Val Gly Lys
 1               5                  10                  15

Ser Thr Ile Phe Asn Arg Ile Ala Gly Glu Arg Ile Ser Ile Val Glu
            20                  25                  30

Asp Thr Pro Gly Val Thr Arg Asp Arg Ile Tyr Ser Ser Ala Glu Trp
        35                  40                  45

Leu Asn Tyr Asp Phe Asn Leu Ile Asp Thr Gly Ile Asp Ile Gly
    50                  55                  60

Asp Glu Pro Phe Leu Ala Gln Ile Arg Gln Gln Ala Glu Ile Ala Met
65                  70                  75                  80

Asp Glu Ala Asp Val Ile Ile Phe Met Val Asn Gly Arg Gly Val
                85                  90                  95

Thr Ala Ala Asp Glu Glu Val Ala Lys Ile Leu Tyr Arg Thr Lys Lys
            100                 105                 110

Pro Val Val Leu Ala Val Asn Lys Leu Asp Asn Thr Glu Met Arg Ala
        115                 120                 125

Asn Ile Tyr Asp Phe Tyr Ser Leu Gly Phe Gly Glu Pro Tyr Pro Ile
    130                 135                 140

Ser Gly Thr His Gly Leu Gly Leu Gly Asp Leu Leu Asp Ala Val Ala
145                 150                 155                 160

Glu His Phe Lys Asn Ile Pro Glu Thr Lys Tyr Asn Glu Glu Val Ile
                165                 170                 175

Gln Phe Cys Leu Ile Gly Arg Pro Asn Val Gly Lys Ser Ser Leu Val
            180                 185                 190
```

```
Asn Ala Met Leu Gly Glu Glu Arg Val Ile Val Ser Asn Val Ala Gly
        195                 200                 205

Thr Thr Arg Asp Ala Val Asp Thr Ser Phe Thr Tyr Asn Gln Gln Glu
    210                 215                 220

Phe Val Ile Val Asp Thr Ala Gly Met Arg Lys Lys Gly Lys Val Tyr
225                 230                 235                 240

Glu Thr Thr Glu Lys Tyr Ser Val Leu Arg Ala Leu Lys Ala Ile Asp
                245                 250                 255

Arg Ser Glu Val Val Ala Val Val Leu Asp Gly Glu Gly Ile Ile
            260                 265                 270

Glu Gln Asp Lys Arg Ile Ala Gly Tyr Ala His Glu Ala Gly Lys Ala
        275                 280                 285

Val Val Ile Val Val Asn Lys Trp Asp Ala Val Asp Lys Asp Glu Ser
    290                 295                 300

Thr Met Lys Glu Phe Glu Glu Asn Ile Arg Asp His Phe Gln Phe Leu
305                 310                 315                 320

Asp Tyr Ala Pro Ile Leu Phe Met Ser Ala Leu Thr Lys Lys Arg Ile
                325                 330                 335

His Thr Leu Met Pro Ala Ile Ile Lys Ala Ser Glu Asn His Ser Leu
            340                 345                 350

Arg Val Gln Thr Asn Val Leu Asn Asp Val Ile Met Asp Ala Val Ala
        355                 360                 365

Met Asn Pro Thr Pro Thr His Asn Gly Ser Arg Leu Lys Ile Tyr Tyr
    370                 375                 380

Ala Thr Gln Val Ser Val Lys Pro Pro Ser Phe Val Val Phe Val Asn
385                 390                 395                 400

Asp Pro Glu Leu Met His Phe Ser Tyr Glu Arg Phe Leu Glu Asn Arg
                405                 410                 415

Ile Arg Asp Ala Phe Gly Phe Glu Gly Thr Pro Ile Lys Ile Phe Ala
            420                 425                 430

Arg Ala Arg Lys
        435

<210> SEQ ID NO 9
<211> LENGTH: 195
<212> TYPE: PRT
<213> ORGANISM: Bacillus subtilis

<400> SEQUENCE: 9

Met Lys Val Thr Lys Ser Glu Ile Val Ile Ser Ala Val Lys Pro Glu
1               5                   10                  15

Gln Tyr Pro Glu Gly Gly Leu Pro Gly Ile Ala Leu Ala Gly Arg Ser
                20                  25                  30

Asn Val Gly Lys Ser Ser Phe Ile Asn Ser Leu Ile Asn Arg Lys Asn
            35                  40                  45

Leu Ala Arg Thr Ser Ser Lys Pro Gly Lys Thr Gln Thr Leu Asn Phe
        50                  55                  60

Tyr Ile Ile Asn Asp Glu Leu His Phe Val Asp Val Pro Gly Tyr Gly
65                  70                  75                  80

Phe Ala Lys Val Ser Lys Ser Glu Arg Glu Ala Trp Gly Arg Met Ile
                85                  90                  95

Glu Thr Tyr Ile Thr Thr Arg Glu Glu Leu Lys Ala Val Val Gln Ile
            100                 105                 110

Val Asp Leu Arg His Ala Pro Ser Asn Asp Asp Val Gln Met Tyr Glu
        115                 120                 125
```

```
Phe Leu Lys Tyr Tyr Gly Ile Pro Val Ile Ile Ala Thr Lys Ala
    130                 135                 140

Asp Lys Ile Pro Lys Gly Lys Trp Asp Lys His Ala Lys Val Val Arg
145                 150                 155                 160

Gln Thr Leu Asn Ile Asp Pro Glu Asp Glu Leu Ile Leu Phe Ser Ser
                165                 170                 175

Glu Thr Lys Lys Gly Lys Asp Glu Ala Trp Gly Ala Ile Lys Lys Met
                180                 185                 190

Ile Asn Arg
        195

<210> SEQ ID NO 10
<211> LENGTH: 346
<212> TYPE: PRT
<213> ORGANISM: Bacillus subtilis

<400> SEQUENCE: 10

Met Lys Thr Lys Arg Trp Phe Val Asp Val Thr Asp Glu Leu Ser Thr
1               5                   10                  15

Asn Asp Pro Gln Ile Ala Gln Ala Ala Leu Leu Arg Glu Asn Glu
            20                  25                  30

Val Val Ala Phe Pro Thr Glu Thr Val Tyr Gly Leu Gly Ala Asn Ala
        35                  40                  45

Lys Asn Thr Asp Ala Val Lys Lys Ile Tyr Glu Ala Lys Gly Arg Pro
50                  55                  60

Ser Asp Asn Pro Leu Ile Val His Ile Ala Asp Ile Ser Gln Leu Glu
65                  70                  75                  80

Asp Leu Thr Gly Pro Ala Pro Glu Lys Ala Lys Thr Leu Met Lys Arg
                85                  90                  95

Phe Trp Pro Gly Ala Leu Thr Leu Ile Leu Pro Cys Lys Pro Asp Ala
                100                 105                 110

Leu Ser Pro Arg Val Thr Ala Gly Leu Glu Thr Val Ala Ile Arg Met
            115                 120                 125

Pro Asp His Pro Leu Ala Leu Ala Leu Ile Arg Glu Ser Gly Leu Pro
130                 135                 140

Ile Ala Ala Pro Ser Ala Asn Leu Ser Gly Lys Pro Ser Pro Thr Lys
145                 150                 155                 160

Ala Glu His Val Ala His Asp Leu Asp Gly Arg Ile Ala Gly Ile Val
                165                 170                 175

Asp Gly Gly Pro Thr Gly Ile Gly Val Glu Ser Thr Val Leu Ser Cys
            180                 185                 190

Ala Asp Asp Ile Pro Val Leu Leu Arg Pro Gly Gly Ile Thr Lys Glu
        195                 200                 205

Gln Ile Glu Ala Val Ile Gly Pro Ile His Val Asp Lys Gly Leu Ser
    210                 215                 220

Asp Gln Asn Glu Lys Pro Ile Ser Pro Gly Met Lys Tyr Thr His Tyr
225                 230                 235                 240

Ala Pro Thr Ala Pro Leu Ala Ile Cys Glu Gly Ser Pro Glu Arg Ile
                245                 250                 255

Gln His Leu Ile Gln Glu Tyr Gln Gln Gly Arg Arg Val Gly Val
            260                 265                 270

Leu Thr Thr Glu Glu Lys Ala Gly Val Tyr Ser Ala Asp Tyr Val Lys
        275                 280                 285

Ser Cys Gly Arg Arg Ala Gln Leu Glu Thr Val Ala Ala Gly Leu Tyr
290                 295                 300
```

-continued

Asp Ala Leu Arg Ser Phe Asp Glu Asn Lys Val Asp Phe Ile Ile Ala
305                 310                 315                 320

Glu Ser Phe Pro Asp Thr Gly Val Gly Leu Ala Ile Met Asn Arg Leu
            325                 330                 335

Met Lys Ala Ala Gly Gly Arg Val Ile Arg
            340                 345

<210> SEQ ID NO 11
<211> LENGTH: 10
<212> TYPE: PRT
<213> ORGANISM: Staphylococcus aureus

<400> SEQUENCE: 11

Leu Pro Val His Ala Asp Gly Pro Ile Ser
1               5                   10

<210> SEQ ID NO 12
<211> LENGTH: 10
<212> TYPE: PRT
<213> ORGANISM: Staphylococcus aureus

<400> SEQUENCE: 12

Leu Lys Ile Phe Lys Tyr Val Ser Leu Ala
1               5                   10

<210> SEQ ID NO 13
<211> LENGTH: 83
<212> TYPE: PRT
<213> ORGANISM: Staphylococcus aureus

<400> SEQUENCE: 13

Met Thr Lys Asp Ile Leu Ile Leu Ala Val Glu Thr Ser Cys Asp Glu
1               5                   10                  15

Thr Ser Val Ser Val Ile Lys Asn Gly Arg Asp Ile Leu Ser Asn Thr
            20                  25                  30

Val Leu Ser Gln Ile Glu Ser His Lys Arg Phe Gly Gly Val Val Pro
        35                  40                  45

Glu Val Ala Ser Arg His His Val Glu Gly Ile Thr Thr Thr Ile Asn
    50                  55                  60

Glu Ala Leu Val Asp Ala Asp Val Ser Met Glu Asp Ile Asp Ala Ile
65                  70                  75                  80

Ala Val Thr

<210> SEQ ID NO 14
<211> LENGTH: 341
<212> TYPE: PRT
<213> ORGANISM: Staphylococcus aureus

<400> SEQUENCE: 14

Met Thr Lys Asp Ile Leu Ile Leu Ala Val Glu Thr Ser Cys Asp Glu
1               5                   10                  15

Thr Ser Val Ser Val Ile Lys Asn Gly Arg Asp Ile Leu Ser Asn Thr
            20                  25                  30

Val Leu Ser Gln Ile Glu Ser His Lys Arg Phe Gly Gly Val Val Pro
        35                  40                  45

Glu Val Ala Ser Arg His His Val Glu Gly Ile Thr Thr Thr Ile Asn
    50                  55                  60

Glu Ala Leu Val Asp Ala Asp Val Ser Met Glu Asp Ile Asp Ala Ile
65                  70                  75                  80

Ala Val Thr Glu Gly Pro Gly Leu Ile Gly Ala Leu Leu Ile Gly Val

```
                    85                  90                  95
Asn Ala Ala Lys Ala Leu Ala Phe Ala Tyr Asp Lys Pro Leu Ile Pro
            100                 105                 110

Val His His Ile Ala Gly His Ile Tyr Ala Asn His Ile Glu Glu Pro
            115                 120                 125

Leu Thr Phe Pro Leu Ile Ala Leu Ile Val Ser Gly His Thr Glu
            130                 135             140

Leu Val Tyr Met Lys Asp His Leu Ser Phe Glu Val Ile Gly Glu Thr
145                 150                 155                 160

Arg Asp Asp Ala Val Gly Glu Ala Tyr Asp Lys Val Ala Arg Thr Ile
                165                 170                 175

Gly Leu Asn Tyr Pro Gly Gly Pro Gln Val Asp Arg Leu Ala Ala Glu
                180                 185                 190

Gly Glu Asp Thr Tyr Ser Phe Pro Arg Val Trp Leu Asp Lys Asp Ser
            195                 200                 205

Tyr Asp Phe Ser Phe Ser Gly Leu Lys Ser Ala Val Ile Asn Gln Leu
            210                 215                 220

His Asn Gln Arg Gln Lys Asn Ile Pro Ile Ile Glu Ala Asn Val Ala
225                 230                 235                 240

Thr Ser Phe Gln Asn Ser Val Val Glu Val Leu Thr Phe Lys Ala Ile
                245                 250                 255

Gln Ala Cys Lys Glu Tyr Ser Val Gln Arg Leu Ile Val Ala Gly Gly
                260                 265                 270

Val Ala Ser Asn Lys Gly Leu Arg Gln Ser Leu Ala Asp Gln Cys Lys
            275                 280                 285

Val Asn Asp Ile Gln Leu Thr Ile Pro Ser Pro Lys Leu Cys Thr Asp
            290                 295                 300

Asn Ala Ala Met Ile Gly Val Ala Gly His Ser Leu Tyr Gln Gln Gly
305                 310                 315                 320

Arg Phe Ala Asp Leu Ala Leu Asn Gly His Ser Asn Ile Asp Leu Glu
                325                 330                 335

Glu Tyr Ser Ala Glu
            340

<210> SEQ ID NO 15
<211> LENGTH: 202
<212> TYPE: PRT
<213> ORGANISM: Staphylococcus aureus

<400> SEQUENCE: 15

Met Met Ile Ile Val Met Leu Leu Leu Ser Tyr Leu Ile Gly Ala Phe
1               5                   10                  15

Pro Ser Gly Phe Val Ile Gly Lys Leu Phe Phe Lys Lys Asp Ile Arg
            20                  25                  30

Gln Phe Gly Ser Gly Asn Thr Gly Ala Thr Asn Ser Phe Arg Val Leu
        35                  40                  45

Gly Arg Pro Ala Gly Phe Leu Val Thr Phe Leu Asp Ile Phe Lys Gly
    50                  55                  60

Phe Ile Thr Val Phe Phe Pro Leu Trp Leu Pro Val His Ala Asp Gly
65                  70                  75                  80

Pro Ile Ser Thr Phe Thr Asn Gly Leu Ile Val Gly Leu Phe Ala
                85                  90                  95

Ile Leu Gly His Val Tyr Pro Val Tyr Leu Lys Phe Gln Gly Gly Lys
            100                 105                 110

Ala Val Ala Thr Ser Ala Gly Val Val Leu Gly Val Asn Pro Ile Leu
```

```
                    115                 120                     125
Leu Leu Ile Leu Ala Ile Ile Phe Phe Ile Val Leu Lys Ile Phe Lys
        130                 135                 140

Tyr Val Ser Leu Ala Ser Ile Val Ala Ala Ile Cys Cys Val Ile Gly
145                 150                 155                 160

Ser Leu Ile Ile Gln Asp Tyr Ile Leu Leu Val Val Ser Phe Leu Val
                165                 170                 175

Ser Ile Ile Leu Ile Ile Arg His Arg Ser Asn Ile Ala Arg Ile Phe
                180                 185                 190

Arg Gly Glu Glu Pro Lys Ile Lys Trp Met
            195                 200

<210> SEQ ID NO 16
<211> LENGTH: 341
<212> TYPE: PRT
<213> ORGANISM: Staphylococcus aureus

<400> SEQUENCE: 16

Met Thr Lys Asp Ile Leu Ile Leu Ala Val Glu Thr Ser Cys Asp Glu
1               5                   10                  15

Thr Ser Val Ser Val Ile Lys Asn Gly Arg Asp Ile Leu Ser Asn Thr
            20                  25                  30

Val Leu Ser Gln Ile Glu Ser His Lys Arg Phe Gly Gly Val Val Pro
        35                  40                  45

Glu Val Ala Ser Arg His His Val Glu Gly Ile Thr Thr Thr Ile Asn
50                  55                  60

Glu Ala Leu Val Asp Ala Asp Val Ser Met Glu Asp Ile Asp Ala Ile
65                  70                  75                  80

Ala Val Thr Glu Gly Pro Gly Leu Ile Gly Ala Leu Leu Ile Gly Val
                85                  90                  95

Asn Ala Ala Lys Ala Leu Ala Phe Ala Tyr Asp Lys Pro Leu Ile Pro
            100                 105                 110

Val His His Ile Ala Gly His Ile Tyr Ala Asn His Ile Glu Glu Pro
        115                 120                 125

Leu Thr Phe Pro Leu Ile Ala Leu Ile Val Ser Gly Gly His Thr Glu
        130                 135                 140

Leu Val Tyr Met Lys Asp His Leu Ser Phe Glu Val Ile Gly Glu Thr
145                 150                 155                 160

Arg Asp Asp Ala Val Gly Glu Ala Tyr Asp Lys Val Ala Arg Thr Ile
                165                 170                 175

Gly Leu Asn Tyr Pro Gly Gly Pro Gln Val Asp Arg Leu Ala Ala Glu
            180                 185                 190

Gly Glu Asp Thr Tyr Ser Phe Pro Arg Val Trp Leu Asp Lys Asp Ser
        195                 200                 205

Tyr Asp Phe Ser Phe Ser Gly Leu Lys Ser Ala Val Ile Asn Gln Leu
    210                 215                 220

His Asn Gln Arg Gln Lys Asn Ile Pro Ile Ile Glu Ala Asn Val Ala
225                 230                 235                 240

Thr Ser Phe Gln Asn Ser Val Val Glu Val Leu Thr Phe Lys Ala Ile
                245                 250                 255

Gln Ala Cys Lys Glu Tyr Ser Val Gln Arg Leu Ile Val Ala Gly Gly
            260                 265                 270

Val Ala Ser Asn Lys Gly Leu Arg Gln Ser Leu Ala Asp Gln Cys Lys
        275                 280                 285

Val Asn Asp Ile Gln Leu Thr Ile Pro Ser Pro Lys Leu Cys Thr Asp
```

```
              290                 295                 300
Asn Ala Ala Met Ile Gly Val Ala Gly His Ser Leu Tyr Gln Gln Gly
305                 310                 315                 320

Arg Phe Ala Asp Leu Ala Leu Asn Gly His Ser Asn Ile Asp Leu Glu
                325                 330                 335

Glu Tyr Ser Ala Glu
                340
```